(12) United States Patent
Potyrailo et al.

(10) Patent No.: US 10,089,850 B2
(45) Date of Patent: *Oct. 2, 2018

(54) SYSTEMS AND METHODS FOR STATUS INDICATION IN A SINGLE-USE BIOMEDICAL AND BIOPROCESS SYSTEM

(71) Applicant: GE Healthcare Bio-Sciences AB, Uppsala (SE)

(72) Inventors: Radislav A. Potyrailo, Niskayuna, NY (US); Klaus Gebauer, Uppsala (SE); Kajsa Stridsberg-Friden, Uppsala (SE); Timothy A. Wortley, Marlborough, MA (US)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/407,244

(22) Filed: Jan. 16, 2017

(65) Prior Publication Data

US 2017/0124845 A1    May 4, 2017

Related U.S. Application Data

(63) Continuation of application No. 14/086,117, filed on Nov. 21, 2013, now Pat. No. 9,571,904.

(51) Int. Cl.
*G08B 21/18*    (2006.01)
*G06K 19/077*    (2006.01)
*G06K 19/07*    (2006.01)

(52) U.S. Cl.
CPC ......... *G08B 21/18* (2013.01); *G06K 19/0702* (2013.01); *G06K 19/0707* (2013.01); *G06K 19/07745* (2013.01)

(58) Field of Classification Search
CPC ...... H04Q 9/00; H04Q 2209/47; G01D 21/00; G06K 19/0717; A61L 2/081;
(Continued)

(56) References Cited

U.S. PATENT DOCUMENTS

2005/0009122 A1* 1/2005 Whelan ................... B01L 3/545
                                                435/7.32
2005/0023137 A1* 2/2005 Bhullar ................... C12Q 1/001
                                                204/403.1
(Continued)

FOREIGN PATENT DOCUMENTS

WO    2009/141369 A1    11/2009

OTHER PUBLICATIONS

Extended European Search Report Received for European Patent Application No. 14864046.9, dated Jul. 21, 2017, 6 pages.

*Primary Examiner* — Mirza Alam
(74) *Attorney, Agent, or Firm* — Wood IP LLC

(57) ABSTRACT

Methods, systems, and apparatus to monitor component status in a bioprocessing environment are disclosed and described. Certain examples provide a sensor device for a disposable bioprocessing component. The example sensor device includes a first portion affixed to the component, the first portion configured to provide an identifier associated with the component. The example sensor device also includes a second portion configured to provide a status indication based on a state of the component. The example sensor device is configured to transmit the identifier and status indication to a control computer associated with a bioprocessing platform including the component.

9 Claims, 13 Drawing Sheets

(58) Field of Classification Search
CPC ......... G06F 15/7842; B01L 2300/0825; G01N 35/00732
USPC ......... 340/870.01, 10.1, 572.7, 572.1, 572.8, 340/10.3, 10.52; 204/401, 403.1; 438/3, 438/57
See application file for complete search history.

(56) References Cited

U.S. PATENT DOCUMENTS

| | | | |
|---|---|---|---|
| 2005/0247782 A1* | 11/2005 | Ambartsoumian | B01L 3/545 235/385 |
| 2006/0244606 A1* | 11/2006 | Li | G08B 13/2417 340/572.7 |
| 2006/0290496 A1* | 12/2006 | Peeters | A61B 5/0002 340/572.1 |
| 2009/0223287 A1* | 9/2009 | Dai | G01N 33/48771 73/64.56 |
| 2009/0273447 A1* | 11/2009 | Selker | A61L 2/0035 340/10.1 |
| 2012/0001731 A1 | 1/2012 | Potyrailo et al. | |
| 2015/0068923 A1* | 3/2015 | Lee | G01N 21/00 205/782 |
| 2015/0137992 A1 | 5/2015 | Potyrailo | |

* cited by examiner

SYSTEMS AND METHODS FOR STATUS INDICATION IN A SINGLE-USE BIOMEDICAL AND BIOPROCESS SYSTEM

RELATED APPLICATIONS

Not Applicable

FEDERALLY SPONSORED RESEARCH OR DEVELOPMENT

Not Applicable

MICROFICHE/COPYRIGHT REFERENCE

Not Applicable

BACKGROUND

Many pharmaceutical and biopharmaceutical laboratory systems now involve single-use bioprocess equipment. Single-use systems provide a lower cost solution than traditional, more expensive, stainless steel systems based on, for example, improved sterility and cleanability, increased cycle time, etc.

Single-use equipment, however, involves many connections between tubing, filters, circuits, disposable components, and the like. Given these connections, there is a need to verify the security and viability of the system components. If connections are not properly made, contamination, leakage, delays, and other errors can negatively impact the process and resulting product.

Currently, connections in a single use system must be verified manually through visual inspections following established checklists and procedures. Rather than continuous monitoring, manually re-checking is required to help ensure continued integrity of the system.

BRIEF SUMMARY

Certain examples provide methods and systems for status monitoring of components in a bioprocessing environment.

Certain examples provide a disposable bioprocessing component including a sensor. The example sensor includes a first portion configured to provide an identifier; and a second portion configured to provide a status indication based on a state of the component. In the example, the identifier and status indication are to be transmitted for use by a control system for a bioprocessing platform.

Certain examples provide a sensor device for a disposable bioprocessing component. The example sensor device includes a first portion affixed to the component, the first portion configured to provide an identifier associated with the component. The example sensor device also includes a second portion configured to provide a status indication based on a state of the component. The example sensor device is configured to transmit the identifier and status indication to a control computer associated with a bioprocessing platform including the component.

Certain examples provide a method to monitor a component in a bioprocessing system including a bioprocessing subsystem and a control subsystem. The example method includes identifying the component based on feedback from a first portion of a sensor associated with the component. The example method includes determining a state of the component based on feedback from a second portion of the sensor associated with the component. The example method includes facilitate triggering of an action based on the state and identification of the component provided wirelessly by the sensor.

Certain examples provide a method of process control by monitoring a component in a bioprocessing system. The example method includes identifying the component based on feedback from a first portion of a sensor associated with the component. The example method includes determining an initial state of the component based on feedback from a second portion of the sensor associated with the component. The example method includes monitoring the process to identify a user action. The example method includes facilitating triggering of an action based on the state and identification of the component provided wirelessly by the sensor.

Figure 1:
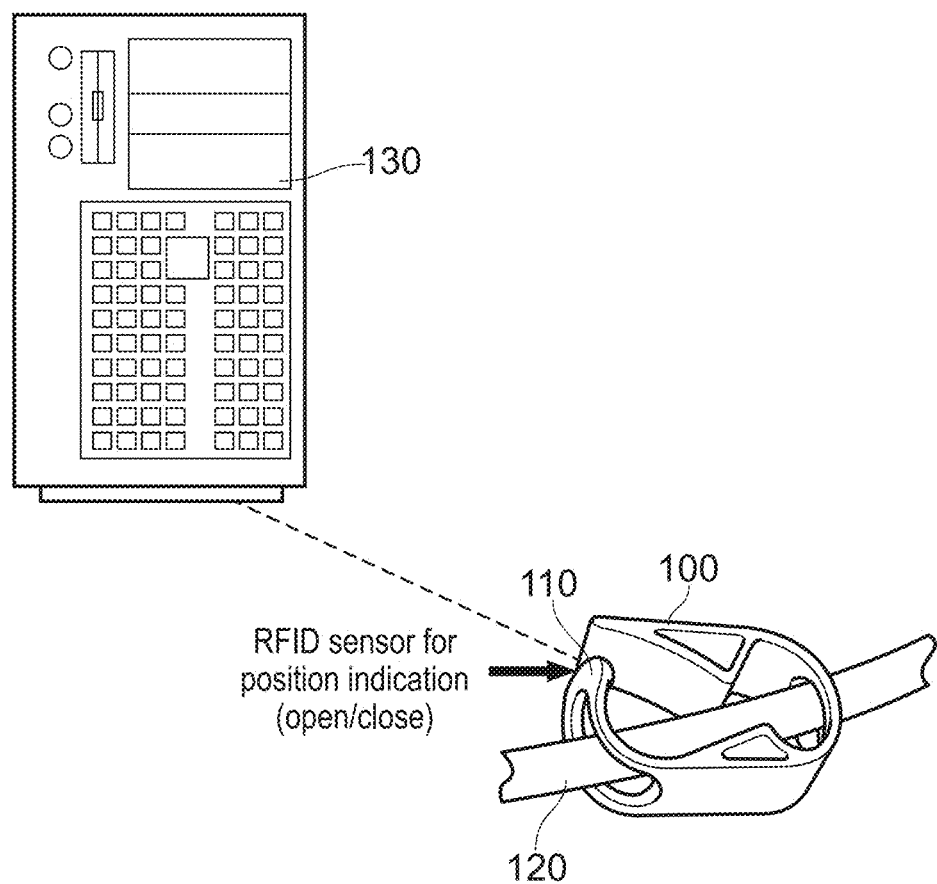
FIGS. 1-3 show example bioprocess system components configured for monitoring.

The foregoing summary, as well as the following detailed description of certain examples of the present invention, will be better understood when read in conjunction the appended drawings. For the purpose of illustrating the invention, certain examples are shown in the drawings. It should be understood, however, that the present invention is not limited to the arrangements and instrumentality shown in the attached drawings.

DETAILED DESCRIPTION OF CERTAIN EXAMPLES

Overview

Certain examples relate to monitoring status and/or state information for a biomedical and/or other bioprocessing system. Example bioprocessing systems and/or applications include biomedical equipment and processes including clinical applications, biopharmaceutical equipment and processing including lab scale process development and large scale production, and the like. Certain examples provide low-resolution sensing for biomedical laboratory systems such as bioreactors, separation, and/or purification (e.g., protein purification) systems (e.g., ÄKTA™ Lab-System Systems sold by GE Healthcare Life Sciences, etc.). Certain examples provide status sensing for single-use and/or other disposable components in a bioprocessing system.

Some examples described herein provide sensors (e.g., radio frequency identification (RFID) and/or other low-resolution (e.g., one-bit sensor) sensor technology) to monitor status/state information of one or more components (e.g., clamp, valve, actuator, switch, lever, etc.) on behalf of a control system for a biomedical or bioprocess unit operation (e.g., UNICORN™ sold by GE Healthcare Life Sciences, etc.). One or more sensors can be mounted to and/or included in a component, such as a tube, clamp, valve, actuator, switch, lever, etc.

For example, a sensor can include a resonant inductor-capacitor-resistor (LCR) sensor such as an RFID sensor (with or without an integrated circuit (IC) memory chip) configured to transmit data via a wireless and/or wired communication path. The LCR sensor can collect data, for example, by collecting an impedance spectrum over a relatively narrow frequency range, such as the resonant frequency range of the LCR circuit.

RFID can be used to refer to a variety of technologies, using different types of radio or magnetic fields to communicate, for example. A basic RFID tag is activated by an external reader and responds with a signal. The signal may include an identifier, a status (e.g., on/off, 0/1, open/closed, etc.). RFID tags or chips can be attached to system components, integrated with system components, positioned near system components (e.g., within centimeters or millimeters of a component being monitored), etc. An RFID reader may communicate with an RFID tag to gather data from the tag and then pass the data along to a control computer, for example. An RFID tag can have read/write capability or only read capability. An RFID tag can have capability to withstand sterilization needed for its application. Nonlimiting examples of sterilization include gamma sterilization, electronic beam sterilization, steam sterilization, gas sterilization, and others known in the art.

An RFID tag or sensor can be used to identify and/or report on a component associated (e.g., attached, positioned near, incorporated in, etc.) with the RFID device. RFID tags or readers and/or wireless sensor nodes (WSNs) can be passive or active (e.g., including a battery) and can, in addition to an identifier (ID) also include a memory, microprocessor, and/or sensor, for example. For example, an RFID tag typically includes at least two components where the first component is an integrated circuit (IC) memory chip to store and process information and modulate and demodulate a radio frequency signal. The memory chip can also be used for other specialized functions, for example it can include a capacitor. It can also include at least one input for an analog signal such as resistance input, capacitance input, or inductance input. A chipless RFID tag may not include an IC memory chip. The chipless RFID tag may be useful in applications where a specific RFID tag does not need to be identified, but rather a signal merely indicating the presence of the tag provides useful information. The second component of the RFID tag is an antenna to receive and transmit the radio frequency signal.

An RFID tag or sensor can also include additional sensing technology such as an antenna that changes its impedance parameters as a function of environmental changes (e.g., pH, temperature, fluid flow, etc.). An analysis of resonance impedance can be used to determine the environmental change. RFID tags/sensors can be active (e.g., proactively broadcasting) or passive (e.g., responsive to query), for example.

Identification, component state, and/or other status information provided by the RFID can include RFID identification, associated component identification, position information, calibration information, and/or other status information, for example. In certain examples, one or more portions of an RFID tag or similar sensor provide an identifier and/or a status indication regarding the tag and/or component associated with and/or otherwise positioned near the tag.

Single-use systems used in biopharmaceutical and medical applications utilize one or more control and/or monitoring system (e.g., UNICORN™ control system sold by GE Healthcare Life Sciences, etc.) to provide controlling and/or monitoring status info ration at the single-use system. For example, components such as tubing clamps (e.g., valves) in a single-use filtration system set-up (e.g., READYTOPROCESS™ (RTP) circuits sold by GE Healthcare Life Sciences, etc.) may be operated manually for the sake of cost, complexity and application flexibility. Nevertheless, a control and monitoring system (e.g., UNICORN™) benefits from status information on actual open/close clamp positions for process control, process records, process safety, etc. Depending on a particular configuration, status information can be provided using wired and/or wireless transmitters, for example.

Status information regarding one or more components in a processing system can help facilitate real-time or substantially real-time control of a bioprocessing system, for example. Monitor signals providing status/state information open or closed, first path or second path, etc.) help enable the system to control process operation. For example, actual flow path and actual valve positions can be displayed in a flow scheme for an operator based on monitoring feedback. A dynamic display helps keep a user informed and updated about a real-time (or substantially real-time) status of a current process run, for example. Supervision and/or control of a process can be facilitated from a local or remote computer based on monitoring feedback. System variables, such as feedback regulation, and definition of system settings, networking, and validation issues can be improved based on monitor status information, for example.

For example, a customer or other user often wishes to verify that bioprocessing equipment has been connected according to instructions outlined in a standard operating procedure (SOP) and/or piping and instrumentation diagram (P&ID). In order to reduce personnel for manual connection verification, technology can provide technical solutions for automated connection verification. Additionally, certain examples can verify that a sealing film at sterile connectors has been removed to help ensure that fluid lines are connected.

An example single-use bioprocessing platforms may include, for example, a mobile standalone biopharmaceutical laboratory, fluid processing cart, etc. For example, GE's ÄKTA™ ready chromatography system provides an automated system, integrated and dedicated for flow path. The platform provides an exchangeable flow path with pump and pinch valves to open and close the flow path. In most examples, tubing is a consumable part that is replaced after a step in the production process for a given pharmaceutical. Automated pinch valves are built into the ÄKTA™ cabinet and controlled by wires. In certain examples, a feedback signal indicating an open or closed valve position is sent by wire to a computer control system.

Single-use technology helps reduce time-consuming device preparations, such as cleaning and cleaning validation, and helps reduce a risk for cross-contamination, which is important in applications such as vaccine manufacturing, for example. For example, GE Healthcare Life Science's READYTOPROCESS™ platform provides disposable, scalable fluid processing solutions. READYTOPROCESS™ connectors, including READYMATE™, Tube Fuser, Tube Sealer, etc., provide aseptic, disposable connections between unit operations, leak proof seals for tubing, etc. READYCIRCUIT™ assemblies include bags, tubing, and connectors to form self-contained purification modules including aseptic paths for processing. Fluid management pathways can be designed and/or customized by an operator, for example, using software provided with the bioprocessing system in conjunction with monitoring feedback. GE Healthcare Life Science's READYKART™ provides a manual fluid processing system on a wheeled cart. Holders and clamps are provided for components of the system. For example, a filter and bag are mounted with a clamp, and pinch clamps are provided with tubing to be manually opened and closed.

In one embodiment, methods and systems to monitor status information on behalf of a control system are disclosed. Status information can include a position (e.g., open/close, etc.) of a component such as a tubing clamp, a valve, etc., and/or any other information that involves low resolution sensing capabilities captured as, for example, a simple ON/OFF signal. The ON/OFF signal can be treated as a threshold or one-bit sensing value, for example. For example, a valve (e.g., a pinch valve, flap valve, ball valve, gate valve, diaphragm valve, etc.) connect to a flexible tubing (and/or integrated in a (semi-) rigid cassette can be associated with a sensor to provide feedback regarding valve position and/or associated actuator state, etc.

Certain embodiments can include multiple sensors providing different pieces of information to a control system (e.g., one sensor providing a component and/or location identification and another sensor providing a status of that component/location, etc.). In another embodiment, a dual-sensor system is disclosed in which a first radio frequency identifier (RFID) tag does not change its status and a second RFID tag changes its status as ON/OFF to provide connection and/or other status verification. For example, a first RFID tag does not change status while providing an identifier while a second tag may change its status irreversibly by breaking an associated electrical circuit (e.g., changing resistance) upon connection. Thus, the first RFID tag provides an identifier this is the sensor associated with valve one in system A) and the second RFID tag provides a status (e.g., valve one is open).

In another embodiment, a verification of connection is performed using two RFID tags, in which one tag is a high frequency (HF) RFID tag that reads correctly when two parts of the tag are in close proximity due to HF radio frequency field interaction. Although a HF tag is discussed as an example, a low frequency (LF) RFID could be used as well. In certain examples, near field communication (NFC) can be used to exchange information when components are in close proximity to each other.

In another embodiment, connection verification is provided based on barcodes and, more specifically, based on alignment of two separate barcodes to be scanned as one combined or integrated barcode. For example, verification of removal of a seal film can be done by barcodes that are initially located inside a tubing or unit-to-unit connection (e.g., a READYMATE™ connection sold by GE Healthcare Life Sciences or other aseptic connection between and/or within unit operation, etc.) which appear when the seal film is pulled out of or otherwise removed from the connection. The barcode is to be readable through the seal film. Additionally, the barcode is to be printed on both sides of the barcode tag (e.g., both on the glue side and on the top side of the tag).

In another embodiment, verification of a connection (e.g., a READYMATE™ connection or other aseptic connection between and/or within unit operation, etc.) is done using a barcode on both sides of the seal film with a hole or opening made through the film for improved readability.

In another embodiment, a verification of seal film removal (e.g., top web seal removal, etc.) is provided in which pulling a sealing film from the connection reveals another barcode, and the operator can scan the barcode to document that the connection (e.g., a READYMATE™ connection or other aseptic connection between and/or within unit operation, etc.) is properly opened.

Although this description discloses embodiments including, among other components, software executed on hardware, it should be noted that the embodiments are merely illustrative and should not be considered as limiting. For example, it is contemplated that any or all of these hardware and software components may be embodied exclusively in hardware, exclusively in software, exclusively in firmware, or in any combination of hardware, software, and/or firmware. Accordingly, certain embodiments may be implemented in other ways.

BRIEF DESCRIPTION

Certain examples provide methods and systems for status monitoring of components in a bioprocessing environment.

Certain examples provide a disposable bioprocessing component including a sensor. The example sensor includes a first portion configured to provide an identifier; and a second portion configured to provide a status indication based on a state of the component. In the example, the identifier and status indication are to be transmitted for use by a control system for a bioprocessing platform.

In certain examples, a single portion can transmit the identifier and/or status indication. In certain examples, the first and second portions are part of the same physical device.

In certain examples of the component, the component includes at least one of a clamp, valve, actuator, switch, connector, and lever (e.g., manually operated, automatically operated, etc.). In certain examples of the component, the status indication includes at least one of a position, a level, and an indication of an open or closed state of the component. In certain examples of the component, the control system is to prompt an action based on the transmitted identifier and status indication, the action comprising at least one of an alert, an alarm, a recording, an instruction to change configuration of the component, and a change in operation of the control system.

In certain examples of the component, the sensor is removably mounted on the component. In certain examples of the components, at least one of the first and second portions of the sensor is integrated in the component. In certain examples of the component, at least one of the first and second portions of the sensor includes a radio frequency identification (RFID) tag. The RFID tag may be a sterilizable RFID tag, for example. Sterilization can be achieved by at least one of gamma irradiation, autoclaving, steam, electron beam, and gas, for example. In certain examples, the RFID tag can include at least one of a high frequency (HF) RFID tag, a low frequency (LF) RFID tag, and a near field communication (NFC) RFID tag. In certain examples of the component, at least one of the first and second portions of the sensor includes a barcode associated with an optical reader.

In certain examples of the component, the first portion of the sensor includes a radio frequency identification tag and the second portion of the sensor includes a wireless sensor node. In certain examples of the component, the second portion activates the first portion to transmit the status indication when the second portion is brought into close proximity with the first portion.

Certain examples provide a sensor device for a disposable bioprocessing component. The example sensor device includes a first portion affixed to the component, the first portion configured to provide an identifier associated with the component. The example sensor device also includes a second portion configured to provide a status indication based on a state of the component. The example sensor device is configured to transmit the identifier and status indication to a control computer associated with a bioprocessing platform including the component.

In certain examples of the device, the component includes at least one of a clamp, valve, actuator, switch, connector, and lever (e.g., manually operated, automatically operated, etc.). In certain examples of the device, the status indication includes at least one of a position, a level, and an indication of an open or closed state of the component. In certain examples of the device, the control computer is to prompt an action based on the transmitted identifier and status indication, the action comprising at least one of an alert, an alarm, a recording, an instruction to change configuration of the component, and a change in operation of the bioprocessing platform.

In certain examples of the device, the sensor device is removably mounted on the component. In certain examples of the device, at least one of the first and second portions of the sensor device is integrated in the component.

In certain examples of the device, at least one of the first and second portions of the sensor device includes a radio frequency identification (RFID) tag. In certain examples of the device, at least one of the first and second portions of the sensor includes a barcode associated with an optical reader.

In certain examples of the device, the first portion of the sensor includes a radio frequency identification tag and the second portion of the sensor includes a wireless sensor node. In certain examples of the device, the second portion activates the first portion to transmit the status indication when the second portion is brought into close proximity with the first portion.

Certain examples provide a method to monitor a component in a bioprocessing system including a bioprocessing subsystem and a control subsystem. The example method includes identifying the component based on feedback from a first portion of a sensor associated with the component. The example method includes determining a state of the component based on feedback from a second portion of the sensor associated with the component. The example method includes facilitate triggering of an action based on the state and identification of the component provided wirelessly by the sensor.

Certain examples provide a method of process control by monitoring a component in a bioprocessing system. The example method includes identifying the component based on feedback from a first portion of a sensor associated with the component. The example method includes determining an initial state of the component based on feedback from a second portion of the sensor associated with the component. The example method includes monitoring the process to identify a user action. The example method includes facilitating triggering of an action based on the state and identification of the component provided wirelessly by the sensor.

Example Systems

As discussed above, (e.g., an RFID tag/sensor, etc.) can be arranged with respect to a component to determine its position, state, and/or other characteristic. For purposes of illustration only, FIG. 1A shows an example tubing clamp 100 into which an RFID sensor 110 has been integrated and/or otherwise placed to determine position of the clamp 100. Other component(s), such as valve(s), switch(es), actuator(s), lever(s), etc., can similarly be monitored. As illustrated in the example of FIG. 1A, one or more RFID 110 or other low-resolution sensor can be used to monitor the status of the clamp 100 with respect to a tube 120. The sensor 110 gathers a position (e.g., open or closed) of the clamp 100 and transmits the information (e.g., a binary or on/off signal, etc.) to an external computer or control system 130. An output or status indicator, such as an on or off signal or one bit value (0 or 1), can be used to indicate to the control system 130 that the clamp 100 is open or closed. Coupled with an identifier associated with the sensor 110 and an association between the sensor 110 and the clamp 100, the control system 130 is able to tell whether the clamp 100 associated with the sensor 110 is open or closed. Alternatively or in addition to RFID, the sensor 110 can respond to an external input such as an applied force or proximity, temperature, solution conductivity, and/or other stimulus, for example.

In certain examples, a low-resolution sensor 110 can provide more than a binary open versus closed or on versus off indication. For example, a component 100 may have five or six steps or positions between being fully open and fully closed to regulate flow and backpressure over a filter in a bioprocess. Component 100 identification and status can be provided by one or more low-resolution sensors 110 to the associated control system 130. For example, a selected flow path can be paired with a bioprocess frame, and a low-resolution wireless sensor can be used to confirm the selected flow path with the control system.

Figure 2A:
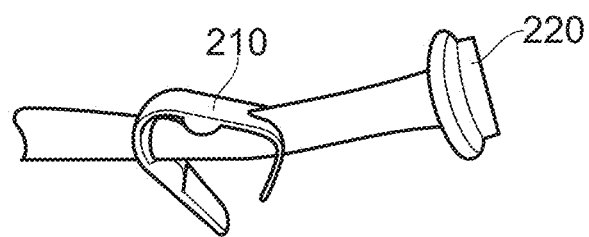
Figure 2B:
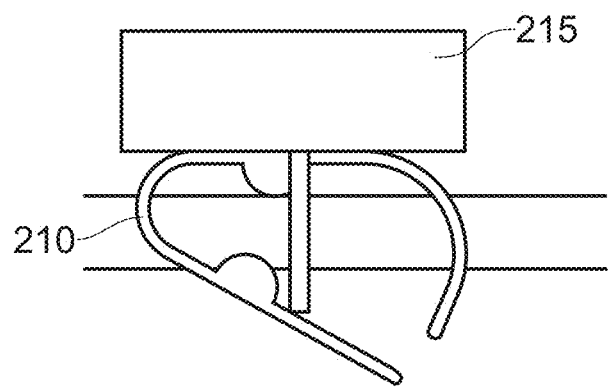

FIG. 2A illustrates a further example of a hose clamp 210 connected to a disposable bioprocess component (e.g., a GE READYCIRCUIT™ tubing assembly) 220. As shown, for example, in FIG. 2B, the hose clamp 210 may include (as in FIG. 1) and/or be associated with (e.g., have mounted on) a wireless sensor network (WSN) node 215. As illustrated in the example of FIGS. 2A-2B, the clamp 210 is equipped with the WSN node 215, which transmits a signal (e.g., a 2.4 GHz and/or other wireless signal) indicating whether the hose clamp 210 is open or closed.

Figure 3:
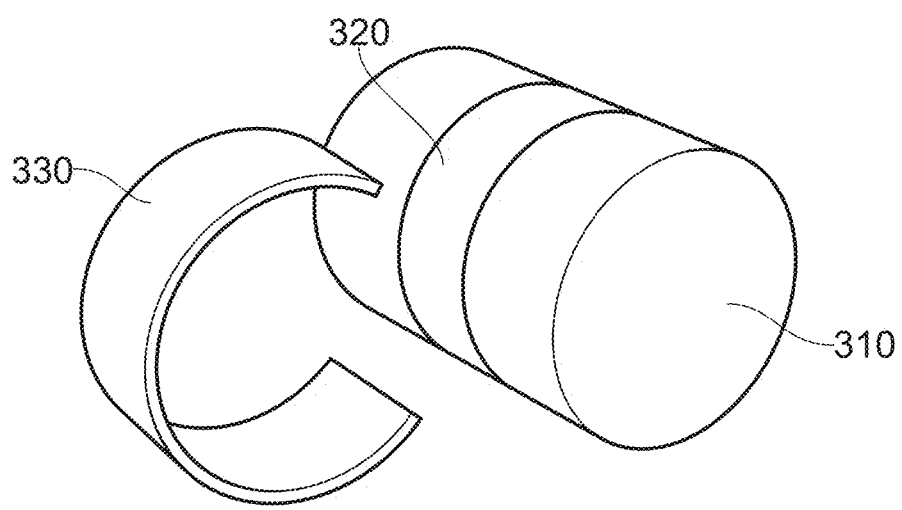

FIG. 3 shows another example bioprocess component 310 monitored using one or more sensors 320, 330. As illustrated in the example of FIG. 3, an RFID tag 320 with optional sensor is molded into the tube 310 (e.g., an antenna and tag provided via winding and/or etching on a flexible printed circuit board, etc.). Alternatively or in addition, the RFID tag 320 may clip or attach onto the tube 310. A clip-on WSN node 330 can be non-permanently mounted close to the RFID tag 320, for example. In the example of FIG. 3, the wireless sensor node 330 provides power to the RFID tag 320 and reads out sensor data from the tag 320. The WSN 330 uses high frequency RFID to communicate with the tag 320 and uses radio and/or other wireless communication (e.g., 2.4 GHz wireless) to communicate with a controller and/or other backbone computer system to provide the sensor data from the RFID tag 320 and/or the WSN 330 itself.

As illustrated in FIGS. 1-3, certain examples provide a low cost control and monitoring system to provide flexibility in movement, assembly, control, monitoring, and documentation. A component transmits a wireless signal to a control system and feeds the control system information about the component's status (e.g., open/closed, connected/disconnected, right path/left path, etc.). While certain examples provide a one-bit or other low-resolution sensor, other examples can provide a plurality of values to indicate intermediate position(s) (e.g., steps between fully open and fully closed for a valve to regulate flow and backpressure over a filter, etc.). Tags/sensors mounted on bioprocessing system components can be equipped with more complex functions than identification only, for example.

In certain examples, a wireless sensor/identification tag can be implemented as a unit. In other examples, a first portion of a wireless sensor/identification tag combination can be integrated into a sterile, disposable component while a second portion is mountable (and perhaps reusable) with respect to the sterile, disposable component. For example, an RFID tag can be provided as a sticker, tape, label, etc., and/or may be formed in the component when the component is manufactured and/or assembled and can be sterilized. A clip-on wireless sensor node can be provided as a reusable unit (e.g., a clamp, ring, etc.), not necessary to sterilize, mounted on the sterile component. A tag and/or sensor can be provided with memory, power, antenna, processor, and/or other capability, for example.

In certain examples, a radiation-hardened, low-cost sensor (e.g., a HF RFID tag) is integrated into a "single use part", and a wireless interface module is (removably) affixed (e.g., clipped on, etc.) to the sensor. The example wireless interface module affixed to the sensor tag includes two wireless interfaces: an RFID antenna communicating with the built in sensor tag (e.g., molded inside the part) and another antenna to communicate with external systems. The interface module can be a rechargeable, reusable module, for example, acting as a gateway for sensor data and transmitting information to a process and/or control system. In certain examples, the module includes and/or is connected to a local battery and provides the built-in sensor with energy through, for example, inductive RFID HF coupling.

Figure 4:
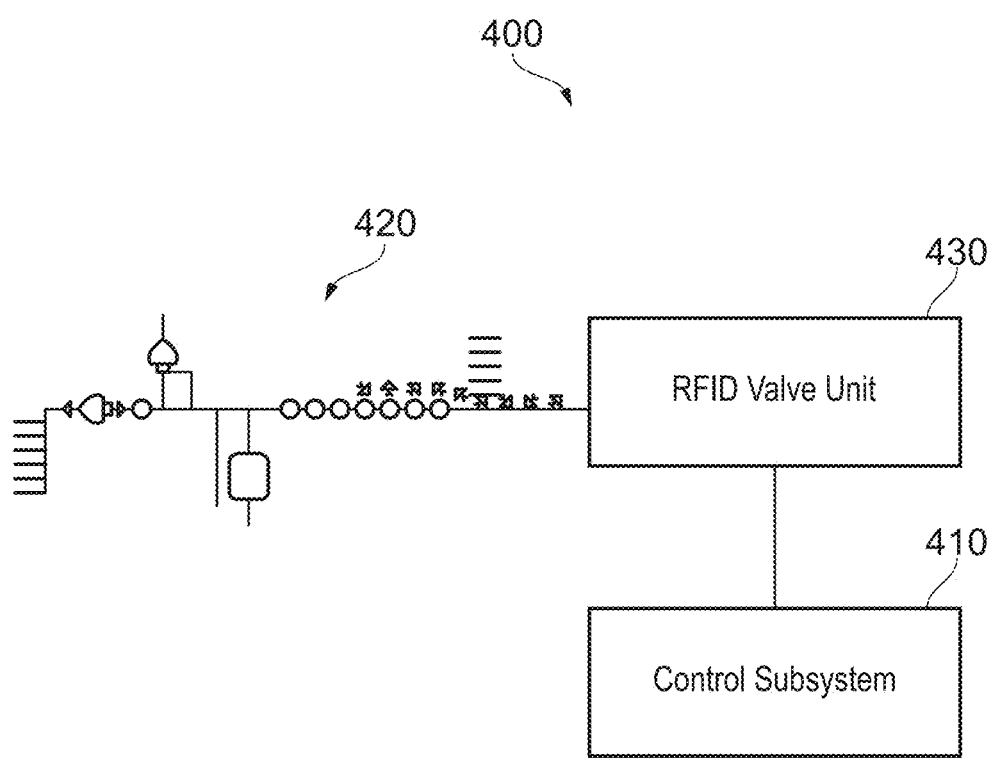
FIG. 4 illustrates an example bioprocess system including a control subsystem for a bioprocessing subsystem.

FIG. 4 illustrates an example bioprocess system 400 including a control subsystem 410 for an associated bioprocessing subsystem 420. An RFID unit 430 is used to identify RFID chips at tubing clamps and/or other components (e.g., actuator, switch, lever, etc.) in the bioprocessing subsystem 420 and map the RFID chips against corresponding positions in the control subsystem 410 P&ID. A status indicator, such as open-close status information, can be read wirelessly (e.g., alone and/or in conjunction with a component and/or sensor identifier) and process control decisions (e.g., pump on or off, etc.) can be made by the control subsystem 410.

In certain examples, a readable range of RFID chips can depend on regulatory requirements and can range from 1 centimeter (cm) to 10 meter (m). In certain examples in which wireless communication is prohibited or otherwise not appropriate, RFID and/or other sensing units can be directly wired to the bioprocess subsystem 420 using reusable or single-use connectors.

In certain examples, a status indicated by an RFID chip can provide information other than an open/closed status. For example, an RFID output can be used to indicate when user interaction is needed to manually change configuration of fluid lines, sampling or sensing devices, etc. With respect to tubing clamps, for example, an RFID sensor is a non-wetted part. However, a sensor can also be provided to detect a status change in a fluid process such as wetting/humidity solution conductivity change, temperature to confirm fluid contact, etc.

In certain examples, low to medium resolution sensing can be employed instead of or in addition to single bit (open/closed, on/off, etc.) status sensing. For example, sensing in discrete steps and/or continuously (e.g., also depending on configuration and capability of the wireless sensor) can provide an indication of a degree of opening for a regulating "proportional control" valve (e.g., using one or more RFID transmitted tier pressure sensors to monitor the proportional control valve). In another example, low to medium resolution sensing can indicate one or more process parameters such as pressure, temperature, conductivity, pH, etc. In another example, low to medium resolution sensing can indicate proximity, position, orientation, elevation, level etc., for one or more bioprocess components and/or in between two or more components.

As illustrated in the example of FIG. 4, one or more sensors, such as RFID tags/sensors 430 can provide wireless and/or wired feedback regarding component position (e.g., position 1, position 2, open, closed, on, off, etc.), identity, and/or other status. In a disposable, single-use system, components are replaced (e.g., per run, daily, frequently, etc.) so that a next process is run with a new component (e.g., a new valve) with a new flow path. Connectivity and proper position in the bioprocess subsystem 420 can be monitored, confirmed, and/or corrected using sensor(s) 430 in conjunction with feedback to (and, in some examples from) the control subsystem 410.

In certain examples, RFID and/or other sensor(s) 430 can also be used to track materials in a factory, production plant, and/or other facility from incoming warehouse management to putting assemblies together and so on and could follow a script or assembly instruction including a list or bill of materials that can be compared against the components in warehouse or preparation room. In certain examples, installation qualification can be facilitated via sensor feedback to help show that parts are put together as intended, and/or operating qualification can be facilitated to help make sure components are functioning as intended. For example, a fixed installation can be manually configured, installation qualification can be facilitated via sensor feedback to the control subsystem 410, operation qualification can be facilitated via sensor feedback to the control subsystem 410, and rapid changeover can be facilitated at startup and/or cleaning time in a single-use system 420.

In certain examples, a reader can be attached to a cart and/or other wheeled/mobile apparatus to facilitate reading of a plurality of sensors 430. The reader can then be wired to the control subsystem 410 and/or wirelessly communicate with the control subsystem 410 to provide status and/or other information from the sensor(s) 430.

Figure 5:
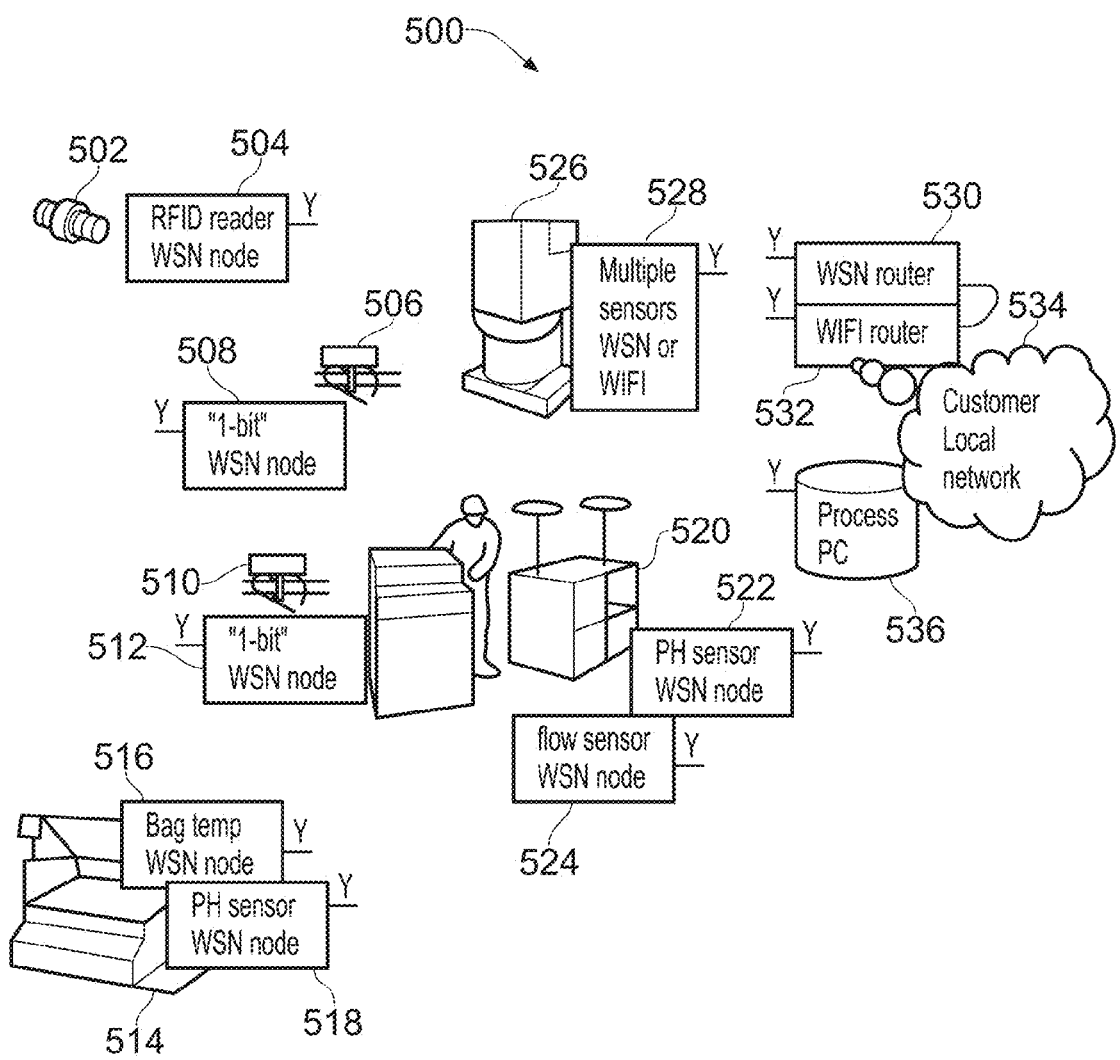
FIG. 5 depicts an example bioprocess infrastructure including a plurality of wireless sensors, tags, and bioprocess components communicating via a local wireless network.

FIG. 5 depicts an example bioprocess infrastructure 500 including a plurality of wireless sensors, RFID tags, and bioprocess components communicating via a local wireless network. The example system 500 includes a connector 502 with an associated RFID reader-WSN combination 504, clamps 506 and 510 and associated one-bit WSNs 508 and 512, a bioreactor 514 and associated bag temperature sensor- WSN combination 516 and pH sensor-WSN combination 518, mobile processing station 520 and associated pH sensor-WSN combination 522 and flow sensor-WSN combination 524, and liquid chromatography system 526 with associated wireless sensor(s) 528. Components of the example system 500 communicate wirelessly via one or more of a wireless sensor network router 530 and a Wi-Fi™ router 532. The routers 530, 532 communicate via a local network 534 to interact with a process and/or control computer 536, for example.

Using the example system 500, data from one or more sensors 504, 508, 512, 516, 518, 577, 524, 528 (such as data from Bioprocess bags, Hose clamp and other physical and chemical sensors) can be acquired using a wireless sensor network (WSN) and/or Wi-Fi network "backbone." The process computer 536 can serve the bioprocess components 502, 506, 510, 514, 520, 526 throughout connection verification, bioprocessing, etc., by collecting data from wireless sensors 504, 508, 512, 528 and can also register physical and/or chemical sensor data from sensors 516, 518, 522, 524, 528, for example. Process information alerts and status can be screened and presented via a user interface, for example.

Figure 6:
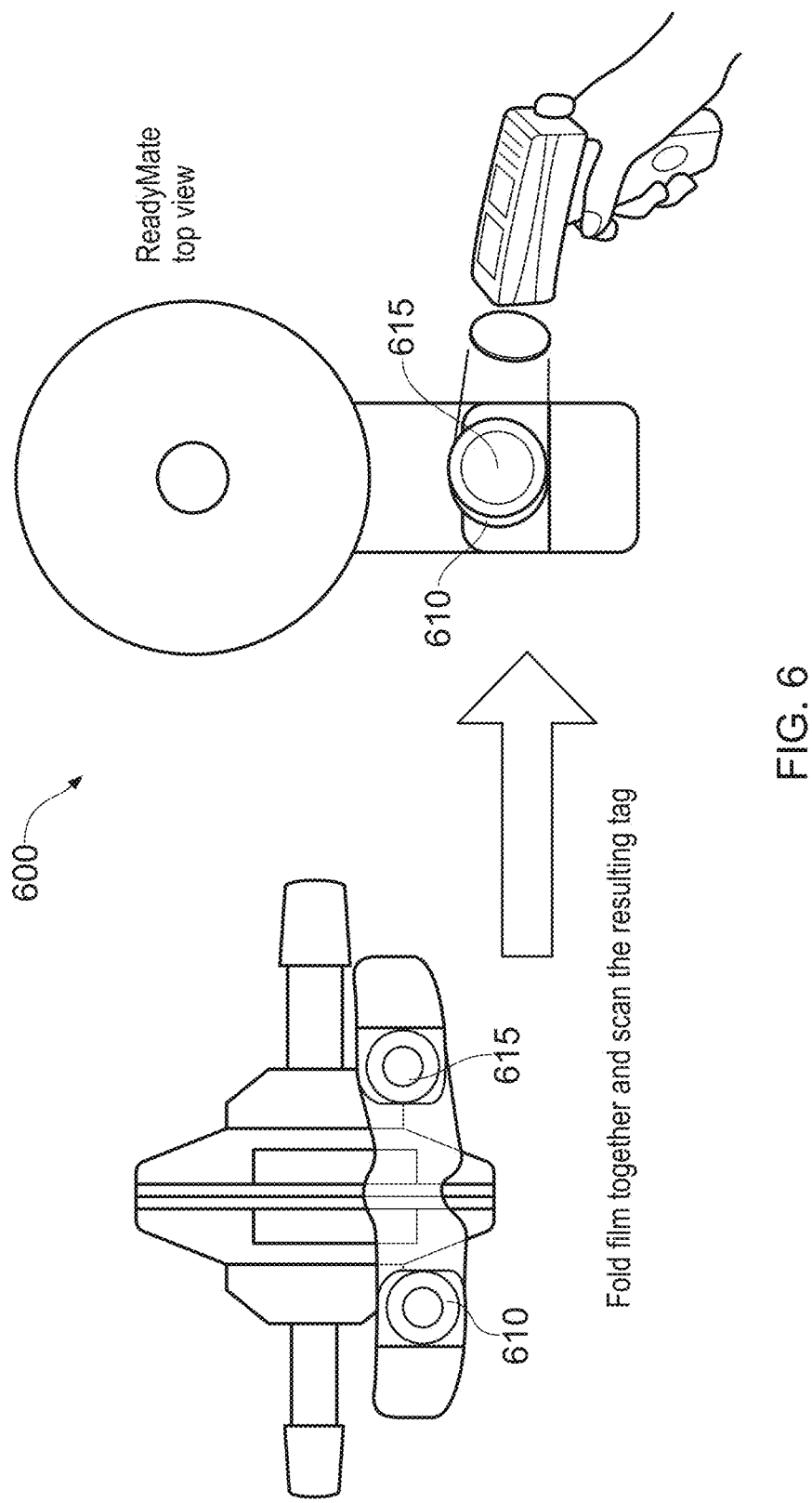
FIG. 6 illustrates another example of connection verification using two RFID tags.

Although certain examples of integrated and/or mounted sensors have been disclosed and described above, a variety of alternative configurations are envisioned. For example, FIG. 6 illustrates another example of connection verification 600 using two RFID tags 610, 615. In the example of FIG. 6, verification of a connection 620 is performed using the two RFID tags 610, 615. As illustrated in the example of FIG. 6, the tags 610, 615 can form two parts of a high frequency (HF) tag. As shown in FIG. 6, the HF tag reads correctly when the two parts of the tag are in close proximity (e.g. due to HF RF field interaction when the tags 610, 615 are positioned together) 630.

Figure 7:
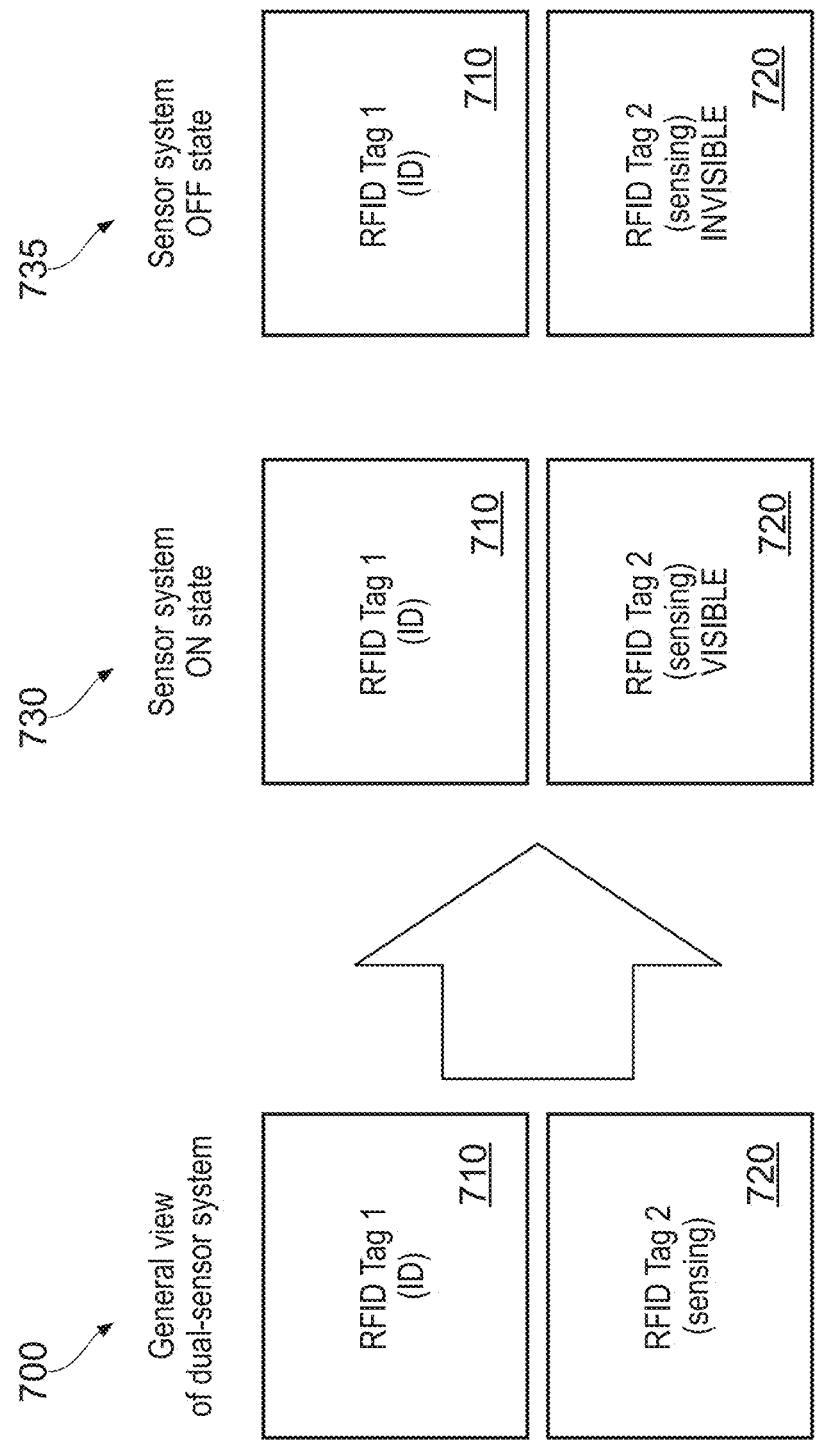
FIG. 7 shows a schematic representation of a dual-sensor system for connect verification.

FIG. 7 shows a schematic representation of a dual-sensor system 700 for connection verification. In the example dual-sensor system 700, two RFID tags 710, 720 provide status information. The first RFID tag 710 does not change its status. The second RFID tag 720 changes its status (e.g., as on or off). In certain examples, the second RFID tag 720 changes its status irreversibly by breaking its electrical circuit (e.g., changing resistance) upon component connection.

As illustrated in the example of FIG. 7, the RFID tag 710 provides an identifier (e.g., associated with a component, a location, a configuration, etc.), and the RFID tag 720 changes state to sense a connection. In an "ON" state 730, the sensing RFID tag 720 is turned on and is therefore visible. In an "OFF" state 735, the sensing RFID tag 720 remains off and is not visible to a detector.

Figure 8:
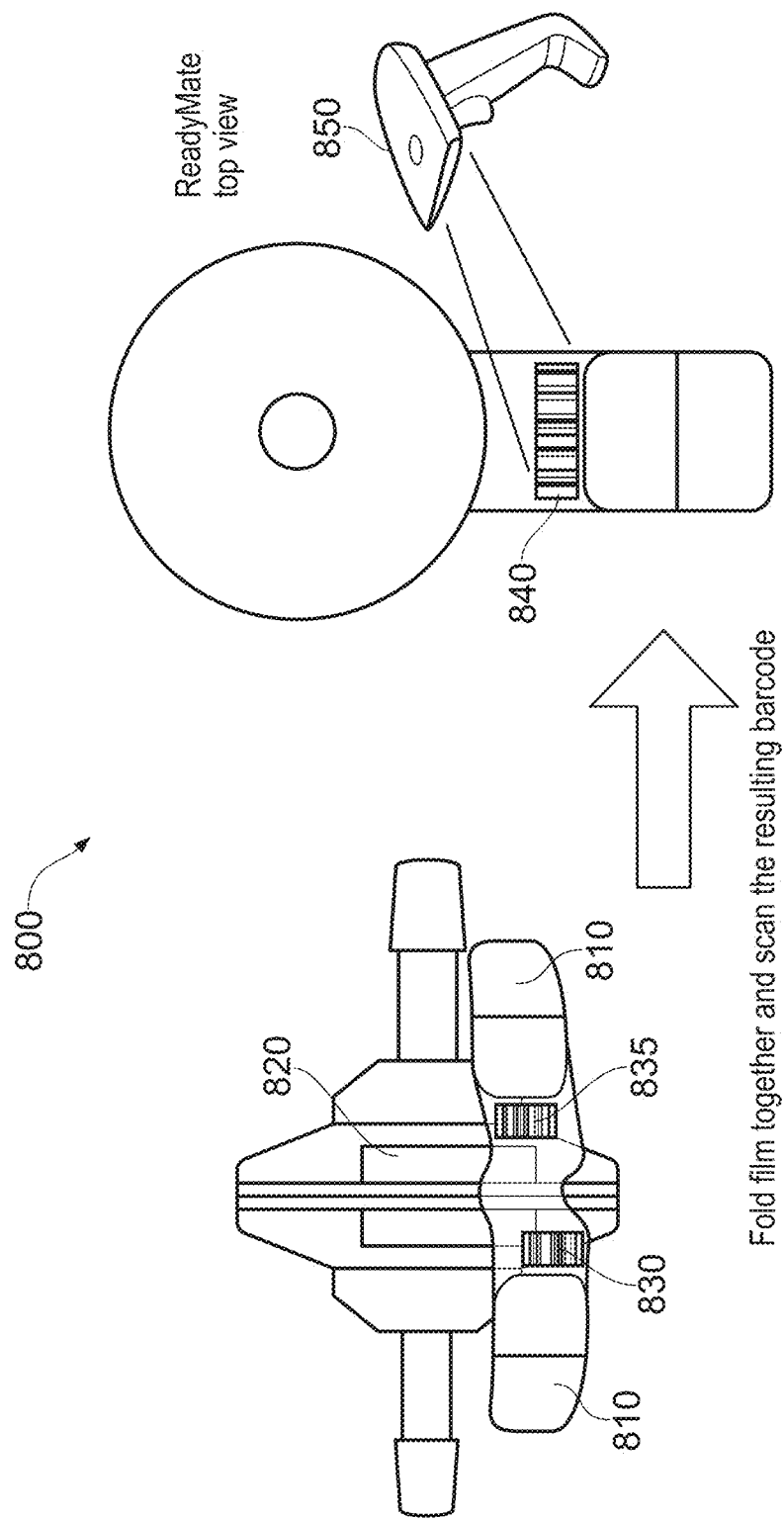
FIG. 8 illustrates an example connection verification solution.

In an embodiment, connection verification is based on barcodes and an ability to align two separate barcodes and scan them as one combined code. Verification of removal of a seal film can be done by barcodes that are initially located inside the aseptic connector (e.g., a READYMATE™ disposable aseptic connector) that appears when the seal film is pulled out of the connection. FIG. 8 illustrates an example connection verification solution 800. A seal film 810 for a tubing connector 820 includes two barcodes 830, 835. A barcode 830, 835 should be readable through the film 810 and be printed on both sides of the barcode tag 830, 835 (e.g., both on the glue side and on the top side of the tag). When the film 810 is pulled out of the connection 820, the barcodes 830, 835, which are initially located inside the connection 820, appear outside the connection 820. The film 810 can be folded together to form a resulting barcode 840 that can be scanned (e.g., using a handheld scanner 850).

Figure 9:
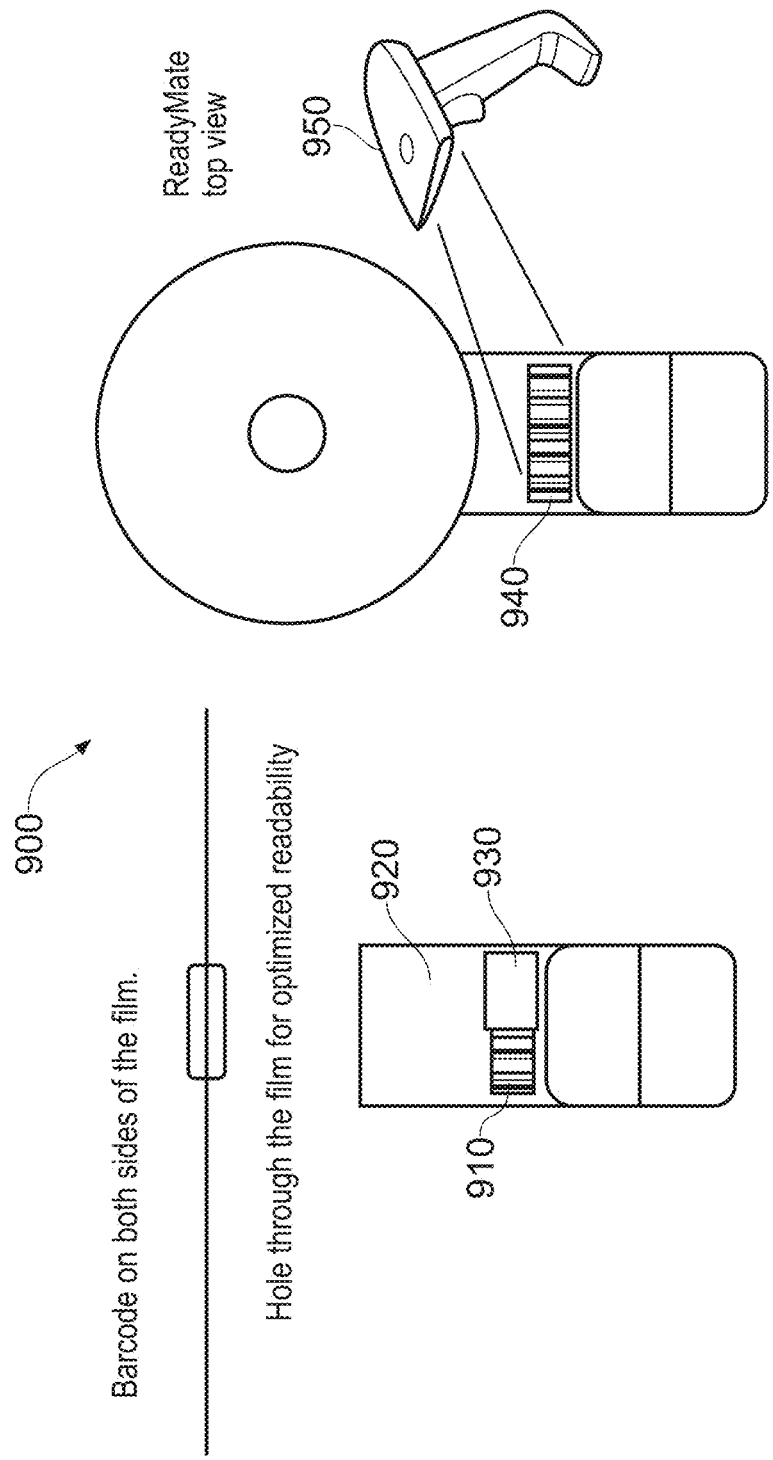
FIG. 9 illustrates an example in which verification of a connection is done with a barcode on both sides of a sealing film and a hole provided through the film.

Another example is illustrated in FIG. 9, in which verification 900 of a connection is done with a barcode 910 on both sides of a sealing film 920, and a hole 930 is provided through the film 920 for improved readability. The combined barcode 940 can then be scanned 950.

Figure 10:
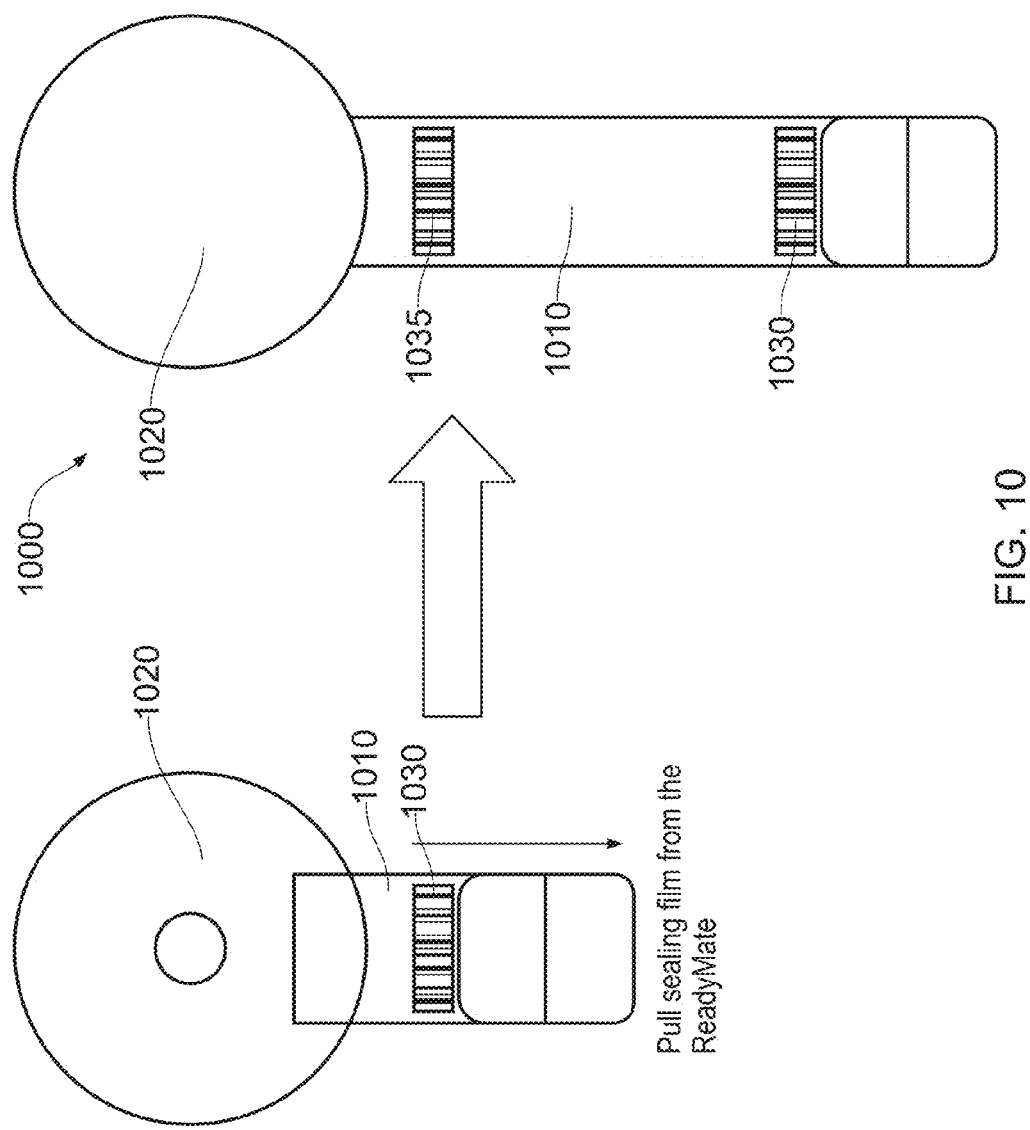
FIG. 10 illustrates an example provides a verification of seal film removal.

FIG. 10 illustrates an example provides a verification 1000 of seal film 1010 removal. In the example of FIG. 10, the sealing film 1010 includes a first barcode 1030. Pulling the sealing film 1010 from the connector 1020 causes a second barcode 1035 to appear when the film is removed from the connector 1020. An operator can scan the barcode 1035 to document that the connector 1020 is properly opened as illustrated in the example of FIG. 10.

Certain examples provide monitoring and control information for a disposables-based technology platform including single-use biomanufacturing and process development products and services (e.g., single-use bioreactors, purification systems, chromatography components, gradient formation and/or dilution circuits, etc.). example, monitoring and status information for components in a biomanufacturing platform can improve reliability and usage of single-use components in the development, manufacture and commercialization of biomolecules in a modular microenvironment.

For example, GE's READYTOPROCESS™ systems include components and instruments for upstream and downstream processing of biopharmaceuticals. The platform includes bioreactors, filters, tubing, connectors, and pre-packed chromatography columns and systems. The platform provides a combination of single-use and multiple-use components such as filters, hoses, connectors, sensors, etc., that can be used by customers to assemble a bioprocess system.

Certain examples provide monitor and control solutions to the components and instruments in the bioprocess platform. Using wireless and/or other electronic identification of single-use passive components hoses, filters, couplers, actuators, switches, levers, valves, clamps, etc.) coupled with sensing of status information related to those components, an associated process control system can be provided with low-cost, accurate, scalable identification and sensing to help support system integrity, stability, and quicker usability. Using wireless sensors in a bioprocess system can help reduce cable complexity and cost and help remove or reduce manual faults. In certain examples, sensors can be integrated into and/or positioned near sterile, single-use parts. In certain examples, two sensors aligned on top of or adjacent to each other with respect to a corrected assembled or otherwise joined component(s) form a combined indicator of component status that changes if the sensors are moved out of proper alignment due to movement of the corresponding component(s).

Example Methods

Figure 11:
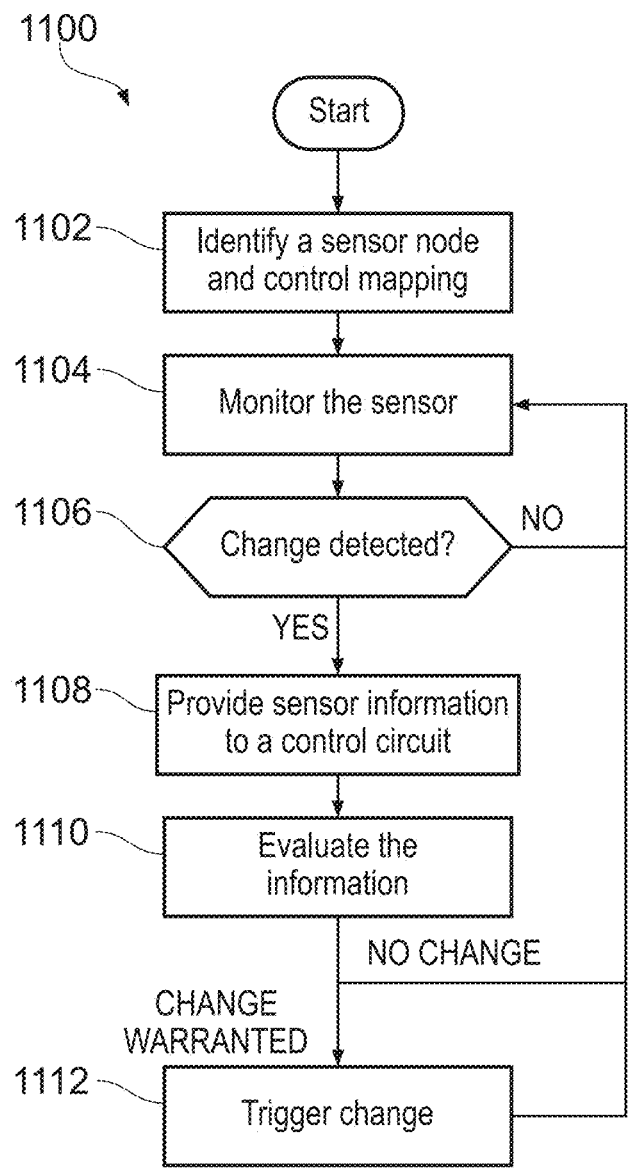
FIG. 11 illustrates a flow diagram of an example method to monitor connection status in a single-use bioprocessing environment.

FIG. 11 illustrates a flow diagram of an example method 1100 to monitor connection status in a single-use bioprocessing platform. At block 1102, a sensor node is identified. For example, a position of a sensor in a processing subsystem (e.g., a selected/configured fluid path, open/closed, etc.) is identified along with a mapping of the sensor to a control subsystem for control and monitoring. The sensor position may be further mapped to a human-machine interface (HMI), such as a process diagram associated with the bioprocessing platform (e.g., a P&ID). For example, a position of an RFID tag with respect to a connector such as a clamp, valve, tubing connector, etc., is identified and indicated in a process map of the bioprocessing system for the control subsystem and its human operator to see. The sensor may also be a BLUETOOTH™ sensor, a Wi-Fi sensor, an NFC sensor, etc. In certain examples, an RFID tag can be associated with a separate wireless communication sensor to power and transmit information related to the RFID tag. In certain examples, the RFID tag can be combined with an antenna or other wireless transmitter. In certain examples, bringing a sensor or other reader in contact or close proximity to a tag (e.g., an RFID tag) provides an identification of that tag (e.g., and its association with a bioprocess component).

At block 1104, the sensor is monitored. For example, a reader/sensor monitors a passive RFID tag for information, or a control system monitors an active RFID chip for an update. For example, the reader (e.g., a wireless sensor node) can provide power and network connectivity to the passive RFID tag associated with the processing system component, for example. Information can include an identification of the component and/or sensor, a detected status (e.g., position, configuration, etc.) of the component, etc. Electrical wires, pneumatic lines, proximity switches, etc., can be used with respect to a sensor/tag combination to provide information regarding a component and transmit the information to a process/control system, for example.

At block 1106, a change in the sensor is detected. For example, a reader pings the sensor and receives new or different information, or the sensor actively provides the updated information. For example, an RFID tag changes from on to off to indicate a valve or clamp has gone from open to closed. As another example, a selected or configured flow path changes from a first path to a second path. As another example, a connection goes from connected to disconnected. In an example, a reader may be attached to a mobile laboratory cart that reads a plurality of sensors and then wired and/or wirelessly transmits information to a control system.

At block 1108, information from the sensor is provided to a control circuit for the bioprocessing platform. For example, the RFID tag embedded in a clamp transmits a wireless signal to the control system with information regarding its status (e.g., open or closed). Information, such as valve identity and valve position (e.g., the identified valve is at position 1, position 2, open, closed, partially open, partially closed, etc.), is provided to the control circuit from the sensor and/or a reader associated with the sensor, for example. Alternatively or in addition, sensor data can include component assembly conflict, operating functionality verification, etc.

At block 1110, the information from the sensor is evaluated by the control circuit. For example, the control system processes the information to detect a value, threshold, abnormality, exception, etc., that would trigger an alert, alarm, change, and/or other action in platform operation and/or configuration. At block 1112, if an action is warranted, then the control circuit triggers an automated change in the bioprocessing platform and/or triggers a request for a manual change to a platform component (e.g., triggers an indicator and/or otherwise sends a message and/or logs a note for an operator, etc.). For example, the control circuit may send an alert for a user to check a connection, replace a component, etc. As another example, the control system may automatically reset a process, trigger an alarm, execute a change or other action according to a pre-defined processing sequence of method by for example increase or decrease flow rate, execute a change or other action in a processing sequence selectable and/or variable in dependence of the input of one or more sensors, etc.

In operation, for example, a consumable component for a biopharmaceutical processing system (e.g., a single-use disposable clamp or valve) is provided. The component may be connected to a battery and/or transmitter that may be reusable or may also be single-use. The component includes a sensing element to detect operation of the component (for exam an opening or closing of a clamp or valve, etc.). A sensor, such as an RFID element integrated or otherwise associated with the component shows or transmits a state of the component (e.g., a binary open/close or a digital state of the element through low-resolution sensing). In certain examples, the consumable components are pre-sterilized (e.g., gamma-radiated) including gamma-compatible RFID tags, gamma-resistant memory, and/or other components.

In certain examples, an energy source (e.g., a clip-on battery cell) is used for transmission of signals to a control system (e.g., to power meter-range RFID signals in conjunction with and/or apart from wireless sensors). In certain examples, a second sensor (e.g., another RFID chip, wireless sensor node, etc.) sits on a monitoring assembly to harvest or collect energy to power the read-out and send back the signal from the primary sensor to the control system.

One or more signals provided may include an identification of a component, component position, component status (e.g., the unit/valve position), an identification of the sensor (e.g., the RFID tag), wireless sensor node, and so on. In certain examples, a combination of multiple sensors (e.g., two or three different RFID tags) can work together, with each sensor customized for a separate purpose (e.g., measure, harvest energy, send out signal, etc.). Multiple sensors or RFID tags can work with different frequencies and configurations/assignments to accommodate one or more subtasks associated with an overall monitoring objective, for example.

In another example, a component, such as a manual tubing clamp, includes a sensor (e.g., a sensing chip), and the control system requests a position of the component. The sensor may be attached to the component at a point of use in a tubing system, for example. An identifier is provided for tubing position to help make sure that errors are reduced or avoided in positioning the component. An identity of the component and the position of the component can be determined using the sensor (e.g., one or more RFID chips and/or other tags), for example. For example, a reader is used to identify the right tubing and place the component in a correct/desired location based on RFID or barcode reading information.

In certain examples, an identifier and status may be monitored and captured for installation and component connection. For example, installation and monitoring of connected parts in a bioprocessing system can be monitored with respect to a valve being mounted to help ensure proper connection and operation of the valve at the point of use with consumable component(s). Additionally, a battery can be mounted with a sensor/transmitter at the point of use. In certain examples, a battery unit is attached to power the valve and is then removed before the user throws away the consumable component(s).

Thus, certain examples provide low cost control systems and methods that provide an operator with flexibility to control, monitor, and document a bioprocessing system, including a mobile bioprocessing system have single-use, disposable components.

Figure 12:
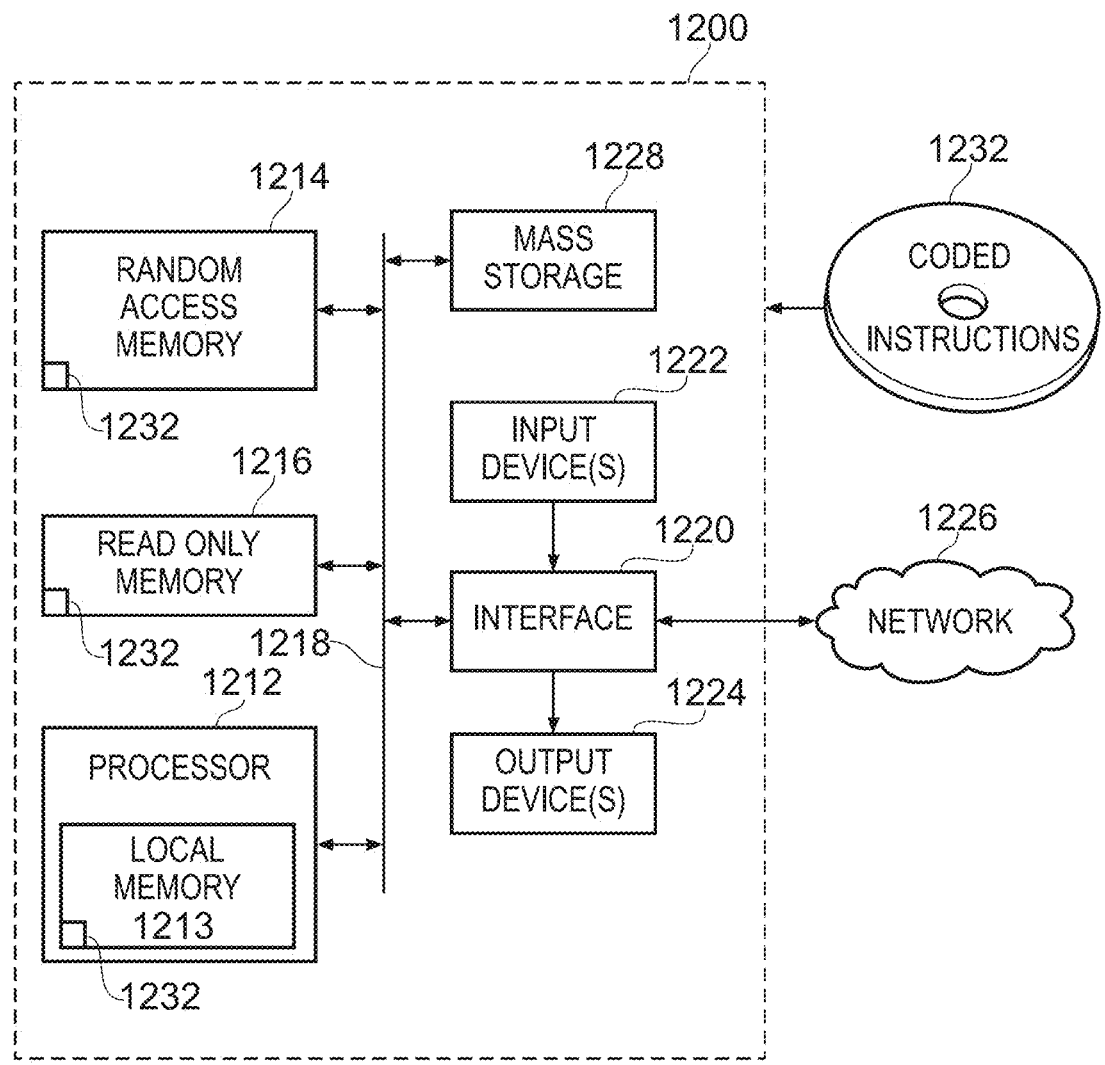
FIG. 12 illustrates a flow diagram of an example method of process control by monitoring a component in a bioprocessing system.

FIG. 12 illustrates a flow diagram of an example method 1200 of process control monitoring a component in a bioprocessing system. At block 1202, a sensor node is identified. For example, a position of a sensor in a processing subsystem (e.g., a selected/configured fluid path, open/closed, etc.) is identified along with a mapping of the sensor to a control subsystem for control and monitoring. In certain examples, a plurality of sensors can be identified (e.g., a plurality of valve sensors in a bioprocess pumping system).

The sensor position may be further mapped to a human-machine interface (HMI), such as a process diagram associated with the bioprocessing platform (e.g., a P&ID). For example, a position of an RFID tag with respect to a connector such as a clamp, valve, tubing connector, etc., is identified and indicated in a process map of the bioprocessing system for the control subsystem and its human operator to see. The sensor may also be a BLUETOOTH™ sensor, a Wi-Fi sensor, an NFC sensor, etc. In certain examples, an RFID tag can be associated with a separate wireless communication sensor to power and transmit information related to the RFID tag. In certain examples, the RFID tag can be combined with an antenna or other wireless transmitter. In certain examples, bringing a sensor or other reader in contact or close proximity to a tag (e.g., an RFID tag) provides an identification of that tag (e.g., and its association with a bioprocess component).

At block 1204, an initial state of the sensor is determined. For example, a reader/sensor monitors a passive RFID tag for information, or a control system monitors an active RFID chip for an update. For example, the reader (e.g., a wireless sensor node) can provide power and network connectivity to the passive RFID tag associated with the processing system component, for example. Information can include an identification of the component and/or sensor, a detected status (e.g., position, configuration, etc.) of the component, etc. Electrical wires, pneumatic lines, proximity switches, etc., can be used with respect to a sensor/tag combination to provide information regarding a component and transmit the information to a process/control system, for example. User interaction (e.g., opening and/or closing of valves, etc.) may be involved to determine initial configuration and status, for example.

At block 1206, process control and associated monitoring begins. Bioprocess system operation continues and is monitored until a change is detected. For example, fluid is pumped through a processing unit until a user action required, requested, and/or desired.

At block 1208, a change in the sensor status is determined. For example, pump action ceases and the user is asked/prompted to change a valve setting (e.g., changing inlet and/or outlet, etc.) while sensor status is monitored. For example, a reader pings the sensor and receives new or different information, or the sensor actively provides the updated information. For example, an RFID tag changes from on to off to indicate a valve or clamp has gone from open to closed. As another example, a selected or configured flow path changes from a first path to a second path. As another example, a connection goes from connected to disconnected. In an example, a reader may be attached to a mobile laboratory cart that reads a plurality of sensors and then wired and/or wirelessly transmits information to a control system. Information, such as valve identity and valve position (e.g., the identified valve is at position 1, position 2, open, closed, partially open, partially closed, etc.), is provided to the control circuit from the sensor and/or a reader associated with the sensor, for example. Alternatively or in addition, sensor data can include component assembly conflict, operating functionality verification, etc.

At block 1210, if a change is detected (e.g., and a corresponding action is warranted), then the control circuit triggers an automated change in the bioprocessing platform and/or triggers a request for a manual change to a platform component (e.g., triggers an indicator and/or otherwise sends a message and/or logs a note for an operator, etc.). For example, the control circuit may send an alert for a user to check a connection, replace a component, etc. As another example, the control system may automatically reset a process, trigger an alarm, execute a change or other action according to a pre-defined processing sequence of method by for example increase or decrease flow rate, execute a change or other action in a processing sequence selectable and/or variable in dependence of the input of one or more sensors, etc.

At block 1212, sensor state is updated following the change. Based on updated information, updated sensor data is obtained. Process operation and control method execution continues (e.g., at block 1206) based on the updated sensor state/status, for example.

Figure 13:
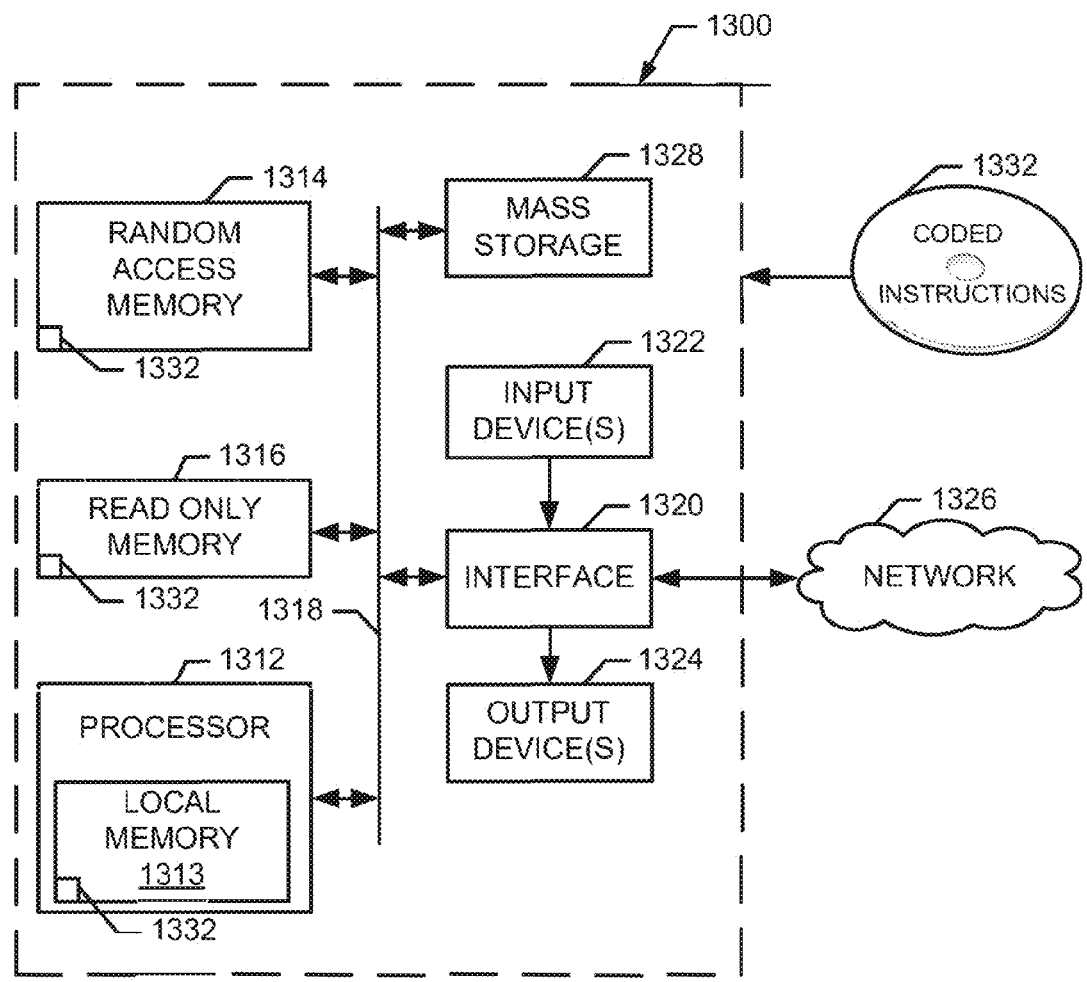
FIG. 13 is a block diagram of an example processor platform that may be used to execute the instructions of FIGS. 11 and 12 to implement the example systems, apparatus, and methods of FIGS. 1-12.

FIG. 13 is a block diagram of an example processor platform 1300 that may be used to execute the instructions of FIGS. 11 and 12 to implement the example systems and methods of FIGS. 1-12. The processor platform 1300 can be, for example, a server, a personal computer, an Internet appliance, a set top box, or any other type of computing device.

The processor platform 1300 of the instant example includes a processor 1312. For example, the processor 1312 can be implemented by one or more microprocessors or controllers from any desired family or manufacturer. The processor 1312 includes a local memory 1313 (e.g., a cache) and is in communication with a main memory including a volatile memory 1314 and a non-volatile memory 1316 via a bus 1318. The volatile memory 1314 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1316 may be implemented by flash memory and/or any other desired type of memory device. Access to the main memory 1314, 1316 is controlled by a memory controller.

The processor platform 1300 also includes an interface circuit 1320. The interface circuit 1320 may be implemented by any type of interface standard, such as an Ethernet interface, a universal serial bus (USB), and/or a PCI express interface.

One or more input devices 1322 are connected to the interface circuit 1320. The input device(s) 1322 permit a user to enter data and commands into the processor 1312. The input device(s) can be implemented by, for example, a keyboard, a mouse, a touchscreen, a track-pad, a trackball, isopoint and/or a voice recognition system.

One or more output devices 1324 are also connected to the interface circuit 1320. The output devices 1324 can be implemented, for example, by display devices (e.g., a liquid crystal display, a cathode ray tube display (CRT), etc.). The interface circuit 1320, thus, typically includes a graphics driver card.

The interface circuit 1320 also includes a communication device such as a modem or network interface card to facilitate exchange of data with external computers via a network 1326 (e.g., an Ethernet connection, a digital subscriber line (DSL), a telephone line, coaxial cable, a cellular telephone system, etc.).

The processor platform 1300 also includes one or more mass storage devices 1328 for storing software and data. Examples of such mass storage devices 1328 include floppy disk drives, hard drive disks, compact disk drives and digital versatile disk (DVD) drives. The mass storage device 1328 may implement a local storage device.

The coded instructions 1332 of FIG. 11 may be stored in the mass storage device 1328, in the volatile memory 1314, in the non-volatile memory 1316, and/or on a removable storage medium such as a CD, DVD or Blu-Ray.

Although certain example methods, systems, apparatus, and articles of manufacture have been described herein, the scope of coverage of this patent is not limited thereto. On the contrary, this patent covers all methods, systems and articles of manufacture fairly falling within the scope of the claims of this patent.

Certain embodiments may include computer readable instructions that are stored in a computer readable medium and executable by a processor. A computer readable medium (or computer readable storage medium) may include various types of volatile and non-volatile storage media, including, for example, random access memory, read-only memory, programmable read-only memory, electrically programmable read-only memory, electrically erasable read-only memory, flash memory, any combination thereof, or any other tangible data storage device. As used herein, the term non-transitory or tangible computer readable medium is expressly defined to include any type of computer readable storage media and to exclude propagating signals.

Some of the described figures depict example block diagrams, systems, and/or flow diagrams representative of methods that may be used to implement all or part of certain embodiments. One or more of the components, elements, blocks, and/or functionality of the example block diagrams, systems, and/or flow diagrams may be implemented alone or in combination in hardware, firmware, discrete logic, as a set of computer readable instructions stored on a tangible computer readable medium, and/or any combinations thereof, for example.

The example block diagrams, systems, and/or flow diagrams may be implemented using any combination of application specific integrated circuit(s) (ASIC(s)), programmable logic device(s) (PLD(s)), field programmable logic device(s) (FPLD(s)), discrete logic, hardware, and/or firmware, for example. Also, some or all of the example methods may be implemented manually or in combination with the foregoing techniques, for example.

The example block diagrams, systems, and/or flow diagrams may be performed using one or more processors, controllers, and/or other processing devices, for example. For example, the examples may be implemented using coded instructions, for example, computer readable instructions, stored on a tangible computer readable medium. A tangible computer readable medium may include various types of volatile and non-volatile storage media, including, for example, random access memory (RAM), read-only memory (ROM), programmable read-only memory (PROM), electrically programmable read-only memory (EPROM), electrically erasable read-only memory (EEPROM), flash memory, a hard disk drive, optical media, magnetic tape, a file server, any other tangible data storage device, or any combination thereof. The tangible computer readable medium is non-transitory.

Further, although the example block diagrams, systems, and/or flow diagrams are described above with reference to the figures, other implementations may be employed. For example, the order of execution of the components, elements, blocks, and/or functionality may be changed and/or some of the components, elements, blocks, and/or functionality described may be changed, eliminated, sub-divided, or combined. Additionally, any or all of the components, elements, blocks, and/or functionality may be performed sequentially and/or in parallel by, for example, separate processing threads, processors, devices, discrete logic, and/or circuits.

While embodiments have been disclosed, various changes may be made and equivalents may be substituted. In addition, many modifications may be made to adapt a particular situation or material. Therefore, it is intended that the disclosed technology not be limited, to the particular embodiments disclosed, but will include all embodiments falling within the scope of the appended claims.

What is claimed is:

1. A bioprocess component comprising:
   a manually operable tubing clamp positionable relative to a flexible fluid tube into a first position for closing the flexible fluid tube by squeezing, or a second position allowing flow within the flexible fluid tube; the manually operable tubing clamp further comprising
   a sensor device operable to (i) monitor an actuation status of the manually operable tubing clamp with respect to the flexible fluid tube wherein the actuation status is indicative of the manually operable tubing clamp being in the first position or the second position, and (ii) indicate to an external control system when the manually operable tubing clamp is in the first position or the second position; and
   an identifier to identify said the manually operable tubing clamp to the external control system;
   wherein the sensor and identifier form part of an RFID circuit for remote communication with said external control system;
   wherein the external control system is arranged to prompt an action based on the transmitted identifier and status indication, the action comprising at least one of a confirmation, an alert, an alarm, a recording, an instruction to change configuration of the component, and a change in operation of the control system.

2. The component of claim 1, wherein the sensor device is removably mounted on the component.

3. The component of claim 1, wherein the sensor device comprises first and second closeable portions at least one of the portions including a radio frequency identification (RFID) tag which changes its status indication in response to said closing.

4. The component of claim 3, wherein the RFID tag comprises a sterilizable RFID tag.

5. The component of claim 4, wherein the is sterilization is at least one of gamma irradiation, autoclaving, steam, electron beam, and gas.

6. The component of claim 5, wherein the RFID tag comprises at least one of a high frequency (HF) RFID tag, a low frequency (LF) RFID tag, and a near field communication (NFC) RFID tag.

7. The component of claim 3, wherein the first portion of the sensor device comprises a radio frequency identification tag and the second portion of the sensor device comprises a wireless sensor node.

8. The component of claim 7, wherein the second portion activates the first portion to transmit the status indication when the second portion is brought into close proximity with the first portion.

9. A method to monitor a component, as claimed in claim 1, in a bioprocessing system including a bioprocessing subsystem and a control subsystem, said method comprising:
  identifying the component based on feedback from a first portion of a sensor device associated with the component;
  determining a state of the component based on feedback from a second portion of the sensor device associated with the component; and
  facilitating triggering of an action based on the state and identification of the component provided wirelessly by the sensor device.

* * * * *